(12) United States Patent  
Juvinall et al.

(10) Patent No.: US 7,010,863 B1
(45) Date of Patent: Mar. 14, 2006

(54) OPTICAL INSPECTION APPARATUS AND METHOD FOR INSPECTING CONTAINER LEAN

(75) Inventors: John W. Juvinall, Ottawa Lake, MI (US); James A. Ringlien, Maumee, OH (US); Stephen M. Graff, Maumee, OH (US); Jie Chen, Ann Arbor, MI (US); William H. Anderson, Holland, OH (US)

(73) Assignee: Owens-Brockway Glass Container Inc., Toledo, OH (US)

( * ) Notice: Subject to any disclaimer, the term of this patent is extended or adjusted under 35 U.S.C. 154(b) by 0 days.

(21) Appl. No.: 10/765,801

(22) Filed: Jan. 26, 2004

(51) Int. Cl.
*G01N 21/00* (2006.01)

(52) U.S. Cl. .................... 33/522; 33/549; 356/428; 356/239.4

(58) Field of Classification Search ............... 33/522, 33/549, 551, 545, 546, 547, 227, 228; 356/428, 356/445, 239.2, 239.3, 239.4, 239.5, 239.6, 356/239.7, 239.8, 240.1
See application file for complete search history.

(56) References Cited

U.S. PATENT DOCUMENTS

| | | | |
|---|---|---|---|
| 3,030,516 A | 4/1962 | Seavey | |
| 3,089,594 A | * 5/1963 | Early | 209/525 |
| 3,180,994 A | 4/1965 | Rottman | |
| 3,302,786 A | 2/1967 | Conrad | |
| 3,662,883 A | 5/1972 | Sager | |
| 3,778,617 A | 12/1973 | Calhoun | |
| 3,827,812 A | 8/1974 | Heimann | |
| 3,932,042 A | 1/1976 | Faani et al. | |
| 3,963,918 A | 6/1976 | Jensen et al. | |
| 4,025,202 A | 5/1977 | Deane | |
| 4,029,958 A | 6/1977 | Wright | |
| 4,083,637 A | 4/1978 | Ellinger et al. | |
| 4,165,939 A | 8/1979 | Woodrow et al. | |
| 4,230,940 A | * 10/1980 | Minami et al. | 250/201.4 |
| 4,249,075 A | 2/1981 | Lovalenti | |
| 4,411,522 A | 10/1983 | O'Conner et al. | |
| 4,433,785 A | 2/1984 | Riggs et al. | |
| 4,435,641 A | 3/1984 | Hajime | |
| 4,500,203 A | 2/1985 | Bieringer | |
| 4,509,075 A | 4/1985 | Simms et al. | |
| 4,553,217 A | 11/1985 | Daudt et al. | |
| 4,580,045 A | 4/1986 | Kulig | |
| 4,608,709 A | 8/1986 | Hedler et al. | |
| 4,664,525 A | 5/1987 | Tagaya | |
| 4,751,386 A | 6/1988 | Gardner | |

(Continued)

FOREIGN PATENT DOCUMENTS

EP 0234105 A1 9/1987

(Continued)

*Primary Examiner*—Diego Gutierrez
*Assistant Examiner*—Amy R. Cohen

(57) ABSTRACT

Apparatus for inspecting lean of a container includes a light source positioned beneath a container for directing light energy onto the container bottom as the container is held in position and rotated around an axis. A light sensor positioned beneath the container receives portions of the light energy from the source reflected from the container bottom. An information processor is coupled to the light sensor for determining, as a combined function of the reflected light energy and container rotation, departure of the container bottom from a plane perpendicular to the axis. The container preferably is held in position and rotated around an axis by a drive roller that urges the container against axially spaced backup rollers so as to define an average axis of rotation as a function of the geometry of the container and spacing between the backup rollers.

21 Claims, 5 Drawing Sheets

U.S. PATENT DOCUMENTS

| | | | |
|---|---|---|---|
| 4,906,098 A * | 3/1990 | Thomas et al. ............. 356/612 |
| 4,908,507 A | 3/1990 | Imre et al. |
| 4,943,713 A | 7/1990 | Yoshida |
| 4,958,223 A | 9/1990 | Juvinall et al. |
| 4,967,070 A * | 10/1990 | Ringlien et al. ........ 250/223 B |
| 5,195,026 A * | 3/1993 | Nonaka et al. ............... 700/47 |
| 5,256,871 A | 10/1993 | Baldwin |
| 5,280,170 A | 1/1994 | Baldwin |
| 5,349,435 A | 9/1994 | Hall et al. |
| 5,354,984 A * | 10/1994 | Baldwin ................. 250/223 B |
| 5,414,939 A * | 5/1995 | Waugaman .................. 33/522 |
| 5,436,722 A | 7/1995 | Baldwin |
| 5,444,237 A | 8/1995 | Takizawa |
| 5,461,228 A | 10/1995 | Kirkman et al. |
| 5,466,927 A | 11/1995 | Kohler et al. |
| 5,486,692 A | 1/1996 | Baldwin |
| 5,489,987 A | 2/1996 | Ringlien |
| 5,499,718 A * | 3/1996 | Bhatia et al. ................ 209/524 |
| 5,510,610 A * | 4/1996 | Baldwin ................. 250/223 B |
| 5,528,026 A | 6/1996 | Burri et al. |
| 5,585,917 A | 12/1996 | Woite et al. |
| 5,637,864 A | 6/1997 | Nicks et al. |
| 5,661,819 A | 8/1997 | Toyama |
| 5,675,516 A | 10/1997 | Bone et al. |
| 5,717,486 A | 2/1998 | Burri et al. |
| 5,730,298 A | 3/1998 | Gernet et al. |
| 5,734,467 A | 3/1998 | Lucas |
| 5,896,195 A | 4/1999 | Juvinall et al. |
| 5,917,602 A * | 6/1999 | Bonewitz et al. ........... 356/614 |
| 5,926,268 A * | 7/1999 | Bonewitz et al. ........ 356/240.1 |
| 6,012,344 A | 1/2000 | Halbo |
| 6,028,302 A | 2/2000 | Wiejak et al. |
| 6,049,379 A | 4/2000 | Lucas |
| 6,089,108 A | 7/2000 | Lucas |
| 6,172,355 B1 * | 1/2001 | Gast et al. .............. 250/223 B |
| 6,198,102 B1 | 3/2001 | Shepherd |
| 6,212,962 B1 | 4/2001 | Lucas |
| 6,256,095 B1 | 7/2001 | Ringlien |
| 6,693,275 B1 * | 2/2004 | Stork et al. ............. 250/223 B |
| 2002/0078769 A1 | 6/2002 | Giometti |
| 2002/0162966 A1 | 11/2002 | Yoder |

FOREIGN PATENT DOCUMENTS

| | | |
|---|---|---|
| EP | 0304164 A2 | 2/1989 |
| EP | 0483966 A2 | 5/1992 |
| EP | 0620430 A1 | 10/1994 |
| GB | 2135452 A | 8/1984 |
| JP | 360113134 A | 6/1985 |
| JP | 401141341 A | 6/1989 |
| JP | 401141342 A | 6/1989 |
| JP | 401213558 A | 8/1989 |
| JP | 405306911 A | 11/1993 |
| JP | 406034573 A | 2/1994 |
| JP | 406034574 A | 2/1994 |
| JP | 406034575 A | 2/1994 |
| JP | 406034576 A | 2/1994 |
| JP | 2004-85512 | 3/2004 |

* cited by examiner

|   | 176 | | Scan | | | | | Transferred |
|---|---|---|---|---|---|---|---|---|
| | 1 | 2 | 3 | 4 | 5 | 6 | 7 | Data |
| | 7 | 6 | 3 | 7 | 20 | 7 | 22 | 22 |
| | 11 | 9 | 9 | 18 | 24 | 6 | 20 | 24 |
| | 23 | 0 | 9 | 22 | 18 | 19 | 20 | 23 |
| | 20 | 23 | 4 | 13 | 2 | 3 | 23 | 23 |
| | 13 | 12 | 12 | 14 | 18 | 21 | 4 | 21 |
| | 78 | 77 | 181 | 213 | 53 | 42 | 112 | 213 |
| | 226 | 7 | 243 | 213 | 248 | 106 | 4 | 248 |
| | 1 | 11 | 2 | 0 | 24 | 22 | 4 | 24 |
| | 15 | 16 | 14 | 23 | 16 | 12 | 16 | 23 |
| | 21 | 1 | 17 | 21 | 2 | 11 | 19 | 21 |
| | 163 | 90 | 247 | 9 | 195 | 14 | 51 | 247 |
| | 16 | 44 | 232 | 150 | 179 | 163 | 120 | 232 |
| | 6 | 17 | 5 | 22 | 24 | 19 | 24 | 24 |
| | 12 | 18 | 19 | 3 | 18 | 0 | 9 | 19 |
| | 11 | 9 | 23 | 19 | 17 | 1 | 2 | 23 |
| | 24 | 23 | 7 | 21 | 22 | 0 | 23 | 24 |
| | 95 | 106 | 89 | 78 | 160 | 122 | 131 | 160 |
| | 10 | 14 | 24 | 7 | 18 | 21 | 21 | 24 |
| | 13 | 11 | 4 | 21 | 3 | 9 | 12 | 21 |
| | 18 | 9 | 18 | 16 | 5 | 0 | 1 | 18 |
| | 5 | 15 | 24 | 8 | 4 | 9 | 23 | 24 |
| | 13 | 6 | 8 | 21 | 3 | 19 | 0 | 21 |
| | 0 | 5 | 8 | 5 | 17 | 19 | 13 | 19 |
| | 23 | 15 | 17 | 11 | 12 | 19 | 11 | 23 |
| | 20 | 5 | 10 | 3 | 1 | 15 | 4 | 20 |
| | 8 | 6 | 2 | 9 | 24 | 5 | 19 | 24 |
| | 7 | 10 | 17 | 3 | 21 | 8 | 18 | 21 |

(brace 178 spans all Scan columns)

OPTICAL INSPECTION APPARATUS AND METHOD FOR INSPECTING CONTAINER LEAN

FIELD OF THE INVENTION

The present invention generally relates to the inspection of articles such as glass containers, and more particularly to an optical inspection apparatus and method for inspecting container lean and other aspects of the container bearing surface.

BACKGROUND OF THE INVENTION

In the manufacture of glass articles, such as glass containers, various anomalies or variations can occur that affect the commercial acceptability of the containers. These anomalies, termed "commercial variations," can involve one of numerous attributes of the container. For example, commercial variations can include dimensional characteristics of the container at the container bottom or bearing surface, at the container finish, or at the container sealing surface, they can also include variations such as stones or checks within the container finish, sidewall or bottom. It is conventional practice to mold indicia on each container that is indicative of the mold of origin of the container for inspection and quality control purposes. Thus, it is often times useful to provide inspection equipment capable of inspecting the containers for commercial variations, mold indicia or other features that warrant inspection. The term "inspection" is used in its broadest sense to encompass any optical, electro-optical, mechanical or electrical observation or engagement with the container to measure or determine a potentially variable characteristic, including but not necessarily limited to mold codes and commercial variations.

An example of an inspection apparatus is shown in U.S. Pat. No. 3,313,409, which discloses an apparatus for inspecting glass containers in which a starwheel conveys containers in sequence through a series of inspection stations. At one of the inspection stations, container lean is inspected by contacting the bearing surface on the container base with a pair of diametrically opposed rollers. As disclosed in U.S. Pat. No. 4,433,785, the rollers are coupled to linear variable differential transformers (LVDTs) to provide signals as the container is rotated. These signals are processed to indicate departure of the bearing surface from a plane and/or departure from perpendicularity to the axis of rotation. Another apparatus for transporting containers through a series of inspection stations is disclosed in U.S. Pat. No. 6,581,751.

Although the inspection apparatus disclosed in the patents noted above, and assigned to the assignee hereof, have enjoyed substantial commercial success, improvements remain desirable. The rollers are in contact with the container bottom, and are subject to mechanical wear and inaccuracy. The sizes of the rollers may limit the sizes of containers with which they can be employed, and they may affect the size (resolution) of variations that can be detected. It is therefore a general object of the present invention to provide an apparatus and method for inspecting containers that address and overcome the aforementioned deficiencies in the art, and can be used for inspecting the bottom or bearing surface of the container.

SUMMARY OF THE INVENTION

The present invention includes a number of aspects, which can be implemented separately from or, more preferably, in combination with each other.

Apparatus for inspecting lean of a container in accordance with one aspect of the present invention includes a light source positioned beneath a container for directing light energy onto the container bottom as the container is held in position and rotated around an axis. A light sensor positioned beneath the container receives portions of the light energy from the source reflected from the container bottom. An information processor is coupled to the light sensor for determining, as a combined function of the reflected light energy and container rotation, departure of the container bottom from a plane perpendicular to the axis. The container preferably is held in position and rotated around an axis by a drive roller that urges the container against axially spaced backup rollers so as to define an average axis of rotation as a function of the geometry of the container and spacing between the backup rollers. In the preferred embodiment, a light source/sensor pair is positioned on diametrically opposed sides of the container bottom, and measurements are made as a function of a comparison of the sensor outputs. This preferred configuration makes the measurement independent of container axial motion.

An optical inspection apparatus for inspecting the bearing surface of a container in accordance with another aspect of the present invention includes a light source, a light sensor and an information processor. The light source is positioned generally beneath the bearing surface and is capable of emitting light that strikes the bearing surface. The light sensor is positioned generally beneath the bearing surface, and is adapted to receive light reflected from the bearing surface and providing a sensor output signal representative of the reflected light. The information processor receives the sensor output signal and utilizes the signal to determine the departure of the bearing surface from a plane that is perpendicular to an axis of the container.

According to a method aspect of the present invention, a container bearing surface is inspected according to the following steps: (a) providing a light source that generally faces the bearing surface, (b) providing a light sensor that generally faces the bearing surface, (c) rotating the container about its axis while maintaining it in an upright position, (d) causing the light source to emit light which reflects from the bearing surface, (e) causing the light sensor to record the position at which the reflected light strikes the light sensor, and (f) analyzing the bearing surface from the position data obtained as the container rotates.

According to another method aspect of the present invention, the amount of data processed during optical inspection of a container bearing surface can be reduced. This method includes the following steps: (a) providing an optical inspection apparatus having a light source, a light sensor, a pre-processor, and a primary processor, (b) causing the light source to reflect light from the bearing surface, (c) causing the light sensor to record the position of the reflected light at a first interval, (d) causing the pre-processor to scan the recorded position data of step (c) at a second interval, wherein the second interval is greater than the first interval, and (e) causing the primary processor to analyze the bearing surface from the scanned data of step (d).

According to another method aspect of the present invention, the bearing surface of a container can be analyzed by optical inspection. This method includes the steps of: (a) providing a first optical probe for inspecting a first point on the bearing surface, (b) providing a second optical probe for inspecting a second point on the bearing surface, (c) causing the first and second optical probes to reflect light off of the bearing surface and record data pertinent to the reflections, (d) utilizing a sinusoidal expression representative of the relative positions of the first and second points, wherein the expression has at least one variable, (e) utilizing a least square fitting technique to solve for the variable, and (f) utilizing the variable to analyze the bearing surface.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF THE PREFERRED EMBODIMENTS

The optical inspection apparatus and method of the present invention may be used to inspect one of any number of types of containers for different criteria, but is particularly well suited for inspecting the bottom or bearing surface of glass containers for container lean. The term "bearing surface" is used in its broadest sense to encompass all container bottom or lower axial surfaces. This includes, but is not limited to, bearing surfaces that are flat, smooth, stipled and/or knurled, as well as those surfaces having circumferentially extending seating rings, where the rings are smooth, stipled and/or knurled.

An example of an indexing and inspection machine that may utilize the optical inspection apparatus and method of the present invention is shown in U.S. Pat. No. 6,581,751, which is incorporated herein by reference. This machine receives a continuous stream of glass articles from an infeed conveyer and transports the articles through a series of angularly spaced inspection stations, each of which examines the container according to different criteria. The indexing and inspection machine includes a first array of gripping fingers mounted on a lower carrier, and a second array of gripping fingers mounted on an upper carrier. Rotation of the carriers with respect to each other causes the finger arrays to grip and release the glassware articles between the individual fingers, while rotation of the carriers conjointly causes them to index the glassware between inspection stations. At least some of the inspection stations include drive rollers for rotating a container about its axis for inspection or other purposes.

Another example of an indexing and inspection machine that could utilize the optical inspection apparatus and method of the present invention is disclosed in U.S. Pat. No. 3,313,409, which was previously mentioned in the background section and is incorporated herein by reference. The apparatus shown in this patent uses a belt conveyer to transport containers along a guideway. In general operation, the containers encounter an indexing head that is circular and has a plurality of circumferentially spaced pockets for receiving the containers. The indexing head is successively indexed to bring each container into position in adjacent inspection stations, which may inspect the containers for various commercial variations and/or other characteristics. After the container has been inspected by each inspection station, the container encounters a discharge station which ejects it onto a conveyer for carrying the container away from the machine. Of course, these are only two examples of machines that may employ the optical inspection apparatus and method of the present invention, as numerous other machines also exist.

Figure 1:
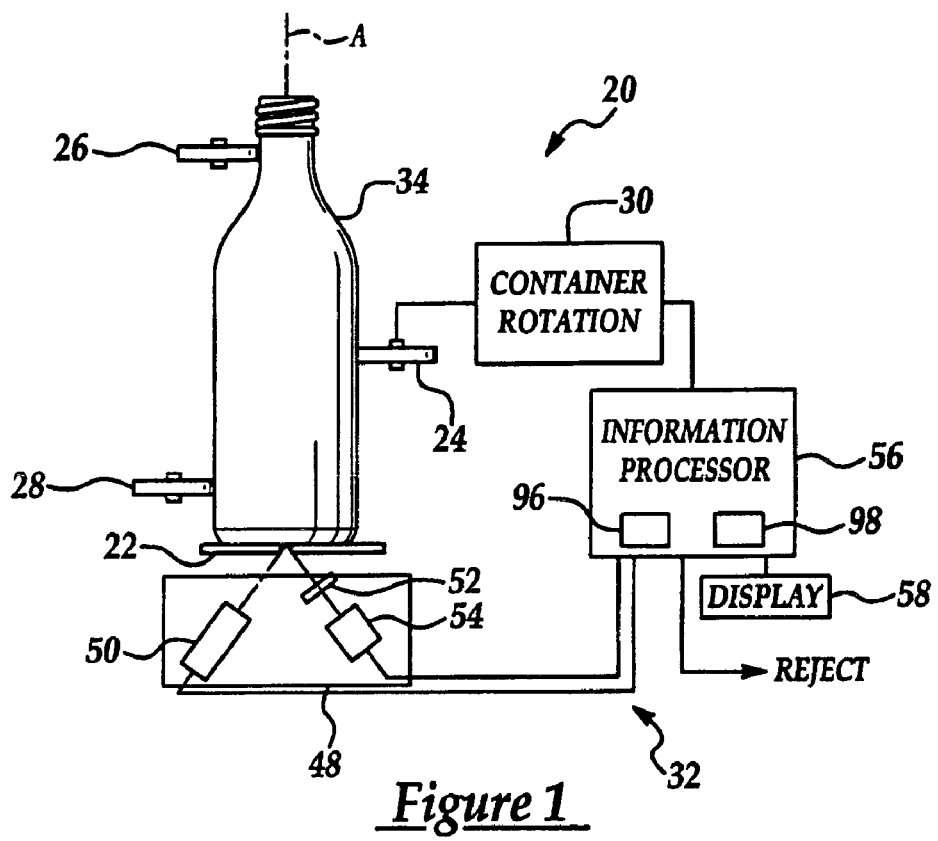
FIG. 1 is a schematic diagram of an inspection station utilizing an embodiment of the optical inspection apparatus of the present invention.
Figure 9A:
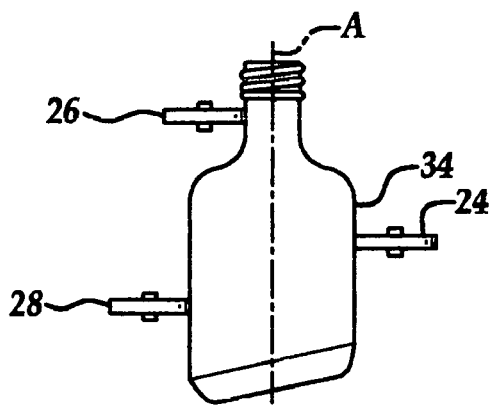
FIGS. 9A and 9B are schematic diagrams that illustrate the effect of container geometry on the average axis of rotation.
Figure 9B:
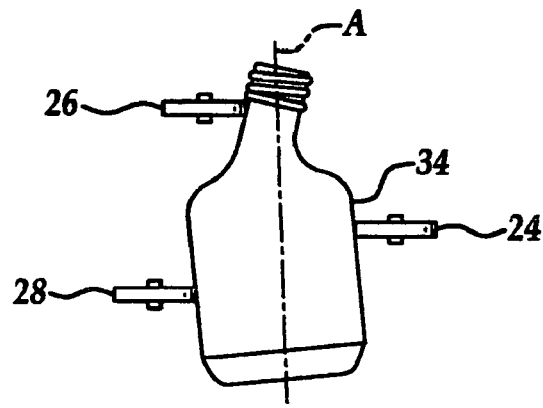

Turning now to FIG. 1, there is shown a schematic diagram of an inspection station 20 which generally includes a drive roller 24, upper and lower free-wheeling backup roller pairs 26, 28, a container rotation controller 30, and an embodiment of an optical inspection apparatus 32 of the present invention. A container 34 under inspection is urged by drive roller 24 against backup rollers 26, 28, and is rotated by drive roller 24 about an average axis of rotation A. Axis A is dependent upon the geometry of container 34 and the spacing between rollers 26, 28. Axis A ideally is colinear with the central axis of the container. Compare, for example, FIG. 9A in which the average axis A is coincident with the container axis but the container bottom is badly tilted, with FIG. 9B in which the container bottom is perpendicular to the container body but the cocked neck on the container skews the average axis of rotation A with respect to the axis of the container body. Drive roller 24 preferably is a servo-motor-driven component that imparts both a radial force and a rotational force to container 34. The radial force squeezes the container between drive roller 24 and free-wheeling backup roller pairs 26, 28, while the rotational force causes container 34 to spin about axis A. Of course, other bottle rotation devices could be used in place of the drive roller. Both the upper and lower free-wheeling roller pairs 26, 28 preferably include two back-up rollers per pair, which together form a V-shaped pocket for rotatably receiving the container and preventing it from being pushed off of the slide plate by drive roller 24.

The apparatus of the invention also preferably, but not necessarily, includes a slide plate 22 on which the container bottom rests during rotation. The slide plate 22 not only provides a plane of reference (FIG. 8) for measurement of container lean, but also supports the container bottom at a position at or near the foci of the measurement optics. It is also envisioned that the slide plate could be eliminated, or the container could be out of contact with the slide plate, and still be within the scope of the invention.

Container rotation controller 30 is operably coupled to drive roller 24 and provides electronic signals to an information processor 56 that are indicative of angular rotation of container 34. This angular rotation information can be based upon fixed angular intervals of rotation, or upon fixed intervals of time during which the rotational velocity of the container is constant. It is also possible for inspection station 20 to include additional components, such as sensors for detecting the presence of a container, other pieces of inspection equipment, etc.

Optical inspection apparatus 32 is a non-contact, optical inspection apparatus that primarily inspects the bearing surface of the container for container "lean", but can also analyze other parameters such as knurl depth, bent container necks, and saddle-shaped or warped bearing surfaces, to name but a few. The "lean" of a container is generally measured by determining the departure of the bearing surface from a plane that is perpendicular to the axis of the container; if the departure exceeds a predetermined amount, then the container can be considered a "leaner." Inspection apparatus 32 preferably includes two optical probes 46 and 48 (FIG. 3), each having a light source 50, a lens system 52 and a light sensor 54, as well as an information processor 56 and an operator display 58. Light sensor 54 includes a sensor array 102, which may be a CCD area array, or more preferably a CCD linear array. A lateral-effect diode sensor can also be used. Although it is preferable that the inspection apparatus have two separate probes that each inspect a separate point on the bearing surface, it is possible, and within the scope of the broadest aspects of the invention, to employ a single optical probe that emits a light beam wide enough to inspect the two different points. The two points on the bearing surface are preferably located at opposite ends of the bearing surface diameter, spaced 180° from each other, as best shown in FIG. 3. For purposes of simplicity, FIGS. 1 and 2 show only one optical probe; however, the discussion of the one probe equally applies to the other. It is also envisioned within the broadest aspects of the invention that a single probe 46 or 48 can be used, with the output thereof compared at 180° increments of rotation.

Figure 2A:
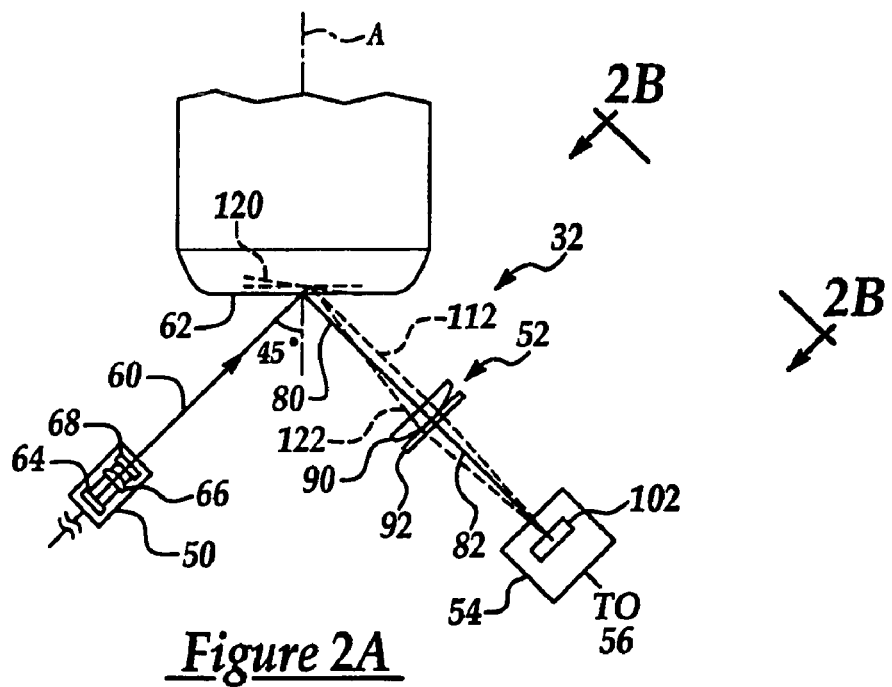
FIGS. 2A and 2B are more detailed schematic diagrams of the optical inspection apparatus of FIG. 1, FIG. 2B being taken from the direction 2B in FIG. 2A.
Figure 2B:
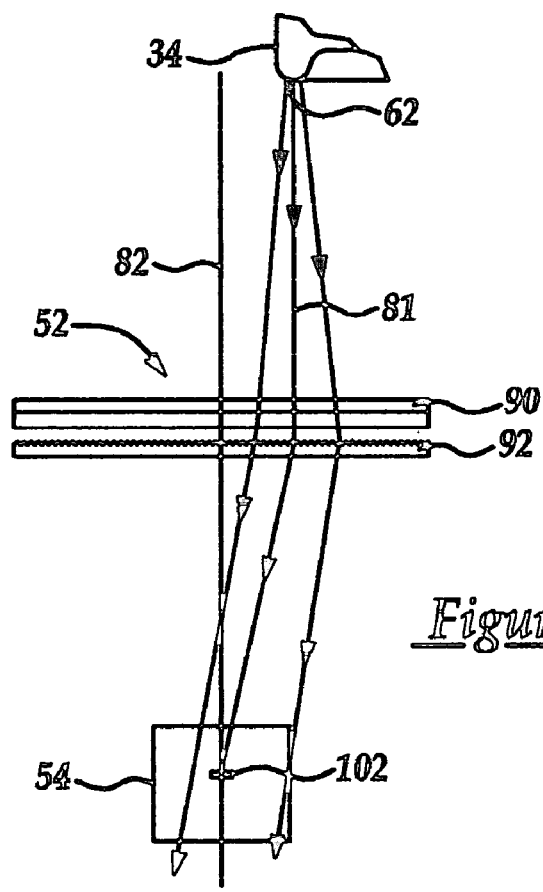
Figure 3:
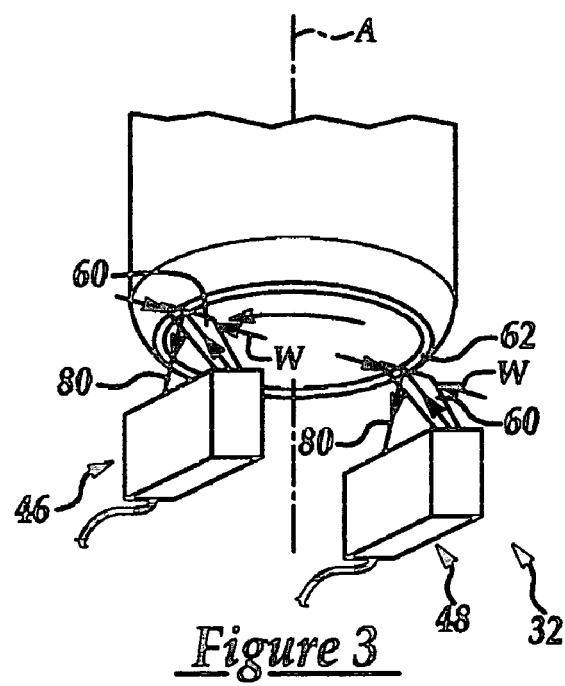
FIG. 3 is a perspective schematic view of the inspection apparatus of FIG. 1.

With reference now to FIGS. 2A, 2B and 3, portions of optical inspection apparatus 32 are shown in greater schematic detail. Light source 50 emits an incident line of light energy 60—i.e., a line-shaped light beam—upwardly at an acute angle such that it impinges upon and reflects from bearing surface 62 of the container. Light source 50 is preferably a structured light source comprising a laser diode 64 for generating a light beam, a lens arrangement 66 for focusing the beam, and a line generator 68 for transforming the beam into a line. In an exemplary embodiment, incident light line 60 is a narrow line of light having a width W, where the beam intersects the container, of approximately 0.75 inch; see FIG. 3. The incident light is at an angle of 45° with respect to axis A, and thereby forms an angle of 90° with respect to a reflected light beam 80.

Lens system 52 (FIGS. 2A and 2B) is positioned between bearing surface 62 and light sensor 54, such that it receives reflected light beam 80, focuses that beam and directs a focused light beam 82 toward the light sensor. Lens system 52 preferably is an anamorphic lens system, and preferably includes a cylindrical lens component 90 positioned adjacent a fresnel or spherical lens component 92. Selection of fresnel or spherical lens 92 is made, at least in part, by its focal length which affects the position of light sensor 54 with respect to the lens system. The lens system is designed to direct certain components of the light reflected from the bearing surface towards the light sensor, while directing other components of the reflected light away from the light sensor. That is, light reflected from incident light line 60 that is parallel to the primary optical axis 82 (FIGS. 2A and 2B) of reflected light beam 80 (FIG. 3), even if the reflected light is slightly spaced from that optical axis (FIG. 2B), will be directed to light sensor 54. In FIG. 2A, reflected light beam 80 on axis 82 is directed onto sensor 54, as is reflected beam 112 parallel to that offset from axis 82. However, beam 122 that is angulated with respect to axis 80, due to tipped surface 120, is refracted onto sensor 54 at the same place that beam 112 strikes the sensor. However, in FIG. 2B, refracted rays 81 parallel to axis 82 are directed onto sensor array 102, while rays on paths 83, 85 non-parallel to axis 82 are directed away from sensor array 102. This feature improves insensitivity to lateral container motion during scanning. These and other optical properties improve the practical attributes of optical inspection apparatus 32, as they allow for small amounts of lateral position error, etc. without rejecting an otherwise acceptable container. Of course, lens system 52 may have additional features and/or components, such as non-reflective coatings, achromatic properties, etc.

Light sensor 54 is positioned beneath bearing surface 62 and near the focal point of lens 92, such that it receives light beams from the lens system and transmits electronic signals representative of the bearing surface position to information processor 56. Light sensor 54 preferably is a camera that includes a linear array sensor 102. The linear array sensor comprises an array of CCD sensing elements or pixels disposed in a line, each of which records the intensity of light striking that pixel by assigning the intensity a numerical value. According to a preferred embodiment, sensor 102 includes 512 linearly aligned pixels. Alternatively, light sensor 54 may include an area array sensor having one or more rows and columns that provide the information processing device with a two-dimensional image, as opposed to a one-dimensional line, of the reflected light. This can be a particularly useful arrangement if the apparatus inspects other parameters of the container. Light sensor 54 can be one of various types cameras, but is preferably a line scan camera such as a Dalsa Orion series high sensitivity line scan camera. Information processor 56 scans the linear array sensor at a constant predetermined interval, either a spatial or a temporal interval, to obtain a picture of the light reflected from bearing surface 62.

Information processor 56 communicates with various components of inspection station 20 and the overall inspection machine, and is capable of analyzing the bearing surface based upon the information received from light sensor 54 of each probe 46, 48. Preferably, the information processor includes one or more inputs and/or outputs for communicating with container rotation controller 30, light source 50 and light sensor 54 of both probes 46, 48, and operator display 58. The information processor also preferably includes first and second electronic processors 96, 98 and a camera controller, to name but a few of the possible components that could be included within the information processor. First processor 96, also referred to as a pre-processor, compresses data from the information provided by light sensor(s) 54 by scanning that information at an interval of container rotation that is greater than the interval at which the processor scans the reflected light. This screening or data compression technique will be explained subsequently in greater detail. Second or primary processor 98 receives the compressed information from pre-processor 96, and executes algorithms and other commands used by the optical inspection apparatus. As will be appreciated by those of ordinary skill in the art, comparable electronic devices and combinations of electronic devices could be used in lieu of the general description of information processor 56 provided above.

In general operation, each of the two probes 46, 48 emits incident light line 60 that strikes a different point on bearing surface 62, and each of the probes records the position of the refracted light beams 82 incident on their respective light sensors 54. A comparison of these two readings allows the inspection apparatus to determine whether or not a container is a "leaner", as well as to determine other parameters of the container. For purposes of simplicity, operation of only one of the two probes will be described, as they both operate in the same general manner. Incident light line 60 and reflected light beam 80 shown in the drawings are aligned along what are referred to as the "nominal optical axes"; that is, the axes of the incident and reflected light under ideal conditions where the bearing surface is contained in a plane perpendicular to rotation axis A. The nominal axes of both the incident and reflected light are angled at 45° to an axis parallel to axis A. The nominal optical axes lie in a plane parallel to axis A. Thus, light sensor 54 generates a stream of data representative of the various reflections from the rotating bearing surface. This stream of data is provided to information processor 56 in the form of a sensor output signal which can be directly sent to primary processor 98 for analysis, or it may first be sent to pre-processor 96 for compression. The primary processor uses the information of the sensor output signal to analyze various parameters of the bearing surface, including container lean and knurl depth. If a container is found to have an unacceptable commercial variation, then that container is flagged as a reject and is removed from the manufacturing process at a downstream station.

Figure 4A:
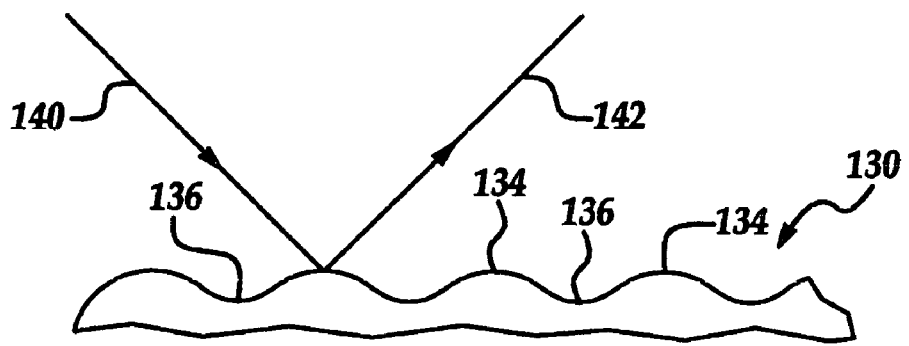
FIGS. 4A–4D pertain to optical inspection of a knurled bearing surface.
Figure 4B:
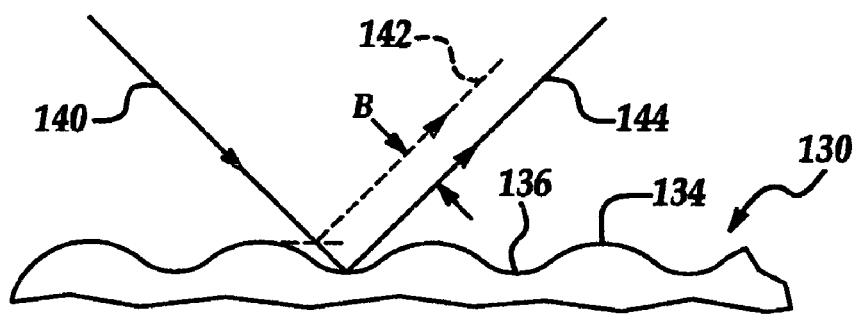
Figure 4C:
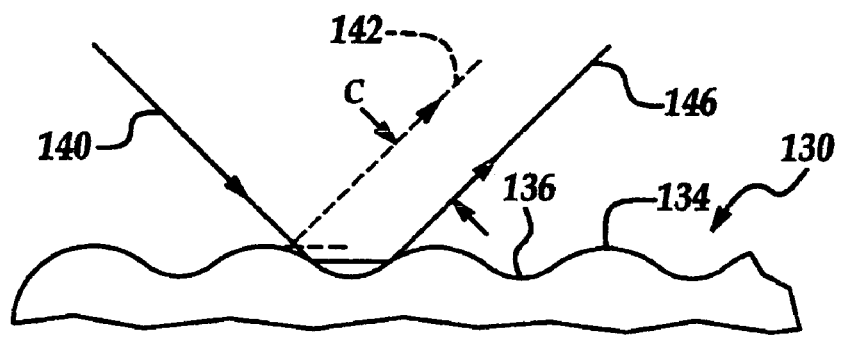
Figure 4D:
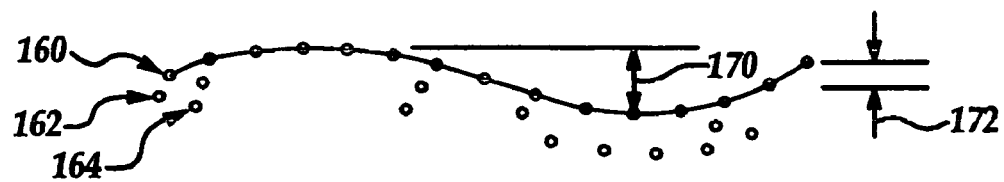

With reference now to FIGS. 4A–4D, optical inspection apparatus 32 is being used to inspect a particular type of bearing surface 130, namely a knurled surface having a series of knurls with peaks 134 and valleys 136. Typically, a knurled surface is used on the bearing surface which extends around the circumference of the container bottom. As the container is rotated, there are only three sections of each knurl that produce reflected beams that actually strike light sensor 54, as all other reflected beams miss the sensor. These three scenarios are represented in FIGS. 4A–4C. In FIG. 4A, incident light 140 is emitted by a light source, reflects from peak 134 such that a reflected beam 142 is directed toward a light sensor. Because incident light 140 reflects from the very tip of peak 134, the light acts as if it has reflected from a planar surface perpendicular to axis A. As shown in FIG. 4B, rotation of the container causes incident light 140 to now strike the knurled surface 130 at a knurl valley 136. As in the previous figure, reflected beam 144 behaves as if it had reflected from a planar surface perpendicular to axis A. However, reflected beam 144 is spaced from reflected beam 142 (shown as a dotted line) by a distance B, such that reflected beam 144 impinges the light sensor at a point different from that of reflected beam 142. FIG. 4C shows the scenario where further rotation of the container causes incident light 140 to strike knurled surface 130 and cause a double reflection from the slopes of adjoining knurls. In this case, incident light 140 is first reflected from a downward slope of a first knurl at an obtuse angle such that it strikes the upward slope of a second adjacent knurl, thus causing a second reflection at an obtuse angle. After reflection from these two sloped surfaces, referred to as a double reflection, reflected beam 146 is directed toward the light sensor and is separated from beam 142 by a distance C. Again, the different paths taken by the reflected beams cause reflected beam 146 to strike the light sensor at a different location from that of beam 142. If the incident beam strikes a knurl at any spot other than these three points, it is reflected from knurl surface 130 in a direction that misses the light sensor. Hence, the reflected light being received by light sensor 54 during container rotation is discontinuous, in that it registers three discreet reflections per knurl. FIG. 4D is a graph that illustrates the output of one of the sensors 54. The points 160 are reflections from knurl peaks (FIG. 4A), the points 162 are reflections from knurl valleys (FIG. 4B), and the points 164 are double reflections from knurl sides (FIG. 4C). Typical glass containers have under two hundred knurls per bearing surface, even though only fifteen knurls are shown here. Distance 170 (FIG. 4D) represents the difference in height between the highest knurl peak and the lowest knurl peak of a particular bearing surface. The difference between the height of these two points is one measure of the tilt of the container with respect to the average axis of rotation, which if divided by the diameter of the bearing surface and multiplied by the container height, can be used to determine the lean of the container according to a technique referred to as the Min/Max method. Distance 172 (FIG. 4D) represents the distance between the peak and valley of a particular knurl, or the knurl depth. The knurl depth can be taken as a single reading, or it can be averaged over a number of readings, etc. The double reflection images 164 are not used in the current implementation of the invention.

Figures 6, 8:
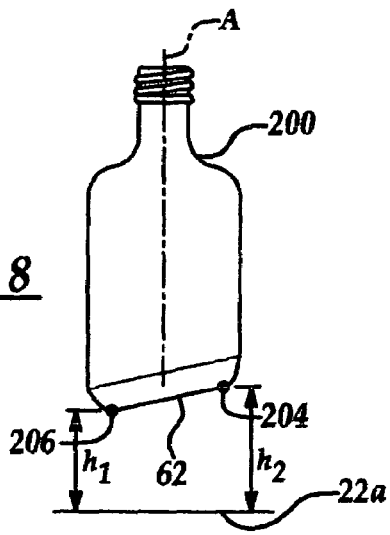
FIG. 6 is a table that illustrates to a method of compressing data from the information gathered by an optical inspection device.
FIG. 8 shows a view of the container that corresponds to a method of analyzing the bearing surface using a least square fitting technique.
Figure 5:
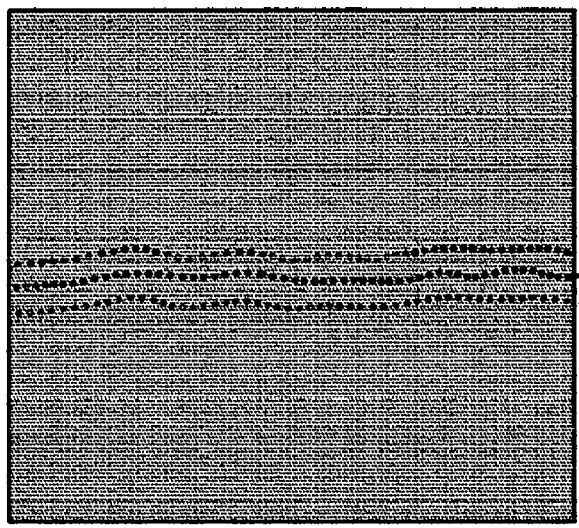
FIG. 5 is a graphic representation of the data in FIG. 4D.
Figure 7:
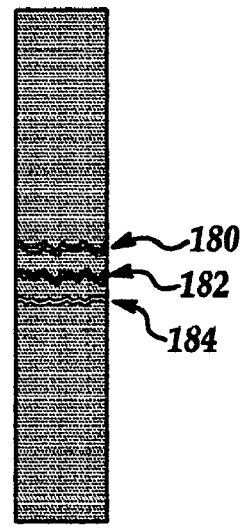
FIG. 7 is a graphic representation of the compressed data of FIG. 6.

FIG. 5 is a schematic representation of a display at 58 (FIG. 1) corresponding to the optical inspections of FIGS. 4A–4D. More specifically, each of the marks on the graph corresponds to an instance where incident light is reflected by the bearing surface and is received by light sensor 54. With reference to FIGS. 6 and 7, there is described a method of compressing the data gathered by light sensor 54 and illustrated in FIG. 5, such that memory and processing strains on the system are minimized. The table of FIG. 6 is divided into columns and rows; at the intersection of each is an individual pixel. The value associated with each individual pixel represents the light intensity of that pixel at a particular point in time. For instance, at scan 1, pixel 1 of linear array sensor 102 registered a '7', pixel 2 an '11', pixel 3 a '23', etc. The light intensity measurements for twenty-seven separate pixels of the linear array sensor were scanned and constitute the first column data in the table. The container is being simultaneously rotated by drive roller 24 so that at a subsequent scan, the linear array sensor records a '6' for pixel 1, a '9' for pixel 2, a '0' for pixel three, and so on. This second scan of the light sensor makes up the contents of the second column. Interval 176 separates successive scans by light sensor 54, and can be based on either a predetermined amount of time or a predetermined angular amount of container rotation. Each row represents the light intensity of a single pixel of linear array sensor 102 during a series of seven scans. At the duration of a larger interval 178, which happens to be seven scans in the present example, pre-processor 106 selects the highest light intensity value for each pixel over those scans; a process referred to as 'sub-scan'. The data contained in the last column, entitled 'transferred data', is the only data that is sent to primary processor 108. Thus, light sensor 54 makes successive scans of the reflected light at first interval 176, while the pre-processor makes successive scans of the light sensor output at a second interval 178 that is greater than the first interval. The optical inspection apparatus of the present invention is able to determine container lean with only a fraction of the data that would otherwise be required, and because the highest intensity value is sent, there is no appreciable decrease in the accuracy of the inspection. As an alternative to selecting the maximum values for each pixel over the scan interval 178, the pre-processor could compute average pixel intensity, etc. Selection of seven scans for data compression likewise is not critical.

A graph representing the sub-scanned information sent by pre-processor 106 according to this method is seen in FIG. 7. The graph of FIG. 7 is a compressed version of the graph of FIG. 5. More specifically, the marks breaking up the various bands 160–164 of FIG. 5 have been removed, thus leaving the condensed, uninterrupted bands 180–184 of FIG. 7. Because the majority of the data being removed corresponds to the spots, there is no loss of significant data and therefore no appreciable loss in accuracy. In the example of a 504-line image, each container is scanned 504 times during a single revolution of the container, or approximately every 0.71°. If data is transferred after every 7$^{th}$ scan, then only 72 lines of data are actually sent to primary processor 108, instead of 504 lines. An object of this method, therefore, is to compress the data for analysis while retaining enough information to accurately perform the inspection. As previously mentioned, the interval between scans by either the light sensor or the pre-processor can be based upon either a predetermined rotational displacement of the container, such as 0.71°, or a predetermined amount of time. This method provides many benefits to optical inspection apparatus 32, including but not limited to, a low false leaner rate, a high rate of catching defects, quicker edge-detection time, and lower memory requirements.

With reference to FIG. 8, there is described another method that may be used by optical inspection apparatus 32 to analyze the bearing surface. This method utilizes a technique referred to as the least square fitting technique. An object of this method is to derive a mathematical expression of the bearing surface 62 that coincides with the measured data taken with respect to a plane 22a (which may be the surface of slide plate 22), and to determine whether or not the container is a leaner from that expression. The mathematical expression used here represents the height differential between two points on the bearing surface, as a function of angular position. The two positions correspond to the positions where probes 46 and 48 impinge the bearing surface with incident light. Container 200 has a bearing surface 62, and two points 204, 206 that are located on the bearing surface 180° apart. The height or axial extent of the points 204 and 206, with respect to reference plane 22a, is referred to as $h_2$ and $h_1$, respectively. As container 200 is rotated about its axis A, the distances $h_1$ and $h_2$ change according to the angular position of the container. In mathematical terms, the difference between heights $h_1$ and $h_2$ can be represented by the following sinusoidal expression:

$$y(I)=h_2(I)-h_1(I)=a_0+a^*\sin(2\pi I/N+\theta_0) \quad \text{(Equation 1);}$$

where $a_0$ is an average axial offset of bearing surface from the plane, a is the amplitude of the sine wave and is the primary variable being solved for, N is the cycle of the sine wave, and $\theta_0$ is the initial phase of the sine wave. It is therefore an object of this method to use the least square fitting technique to calculate a value for 'a' so that the expression above best models the measured data provided by light sensor 54. A linearization of expression (1) makes it easier to apply the least square fitting technique to the measured data, and yields the value of a:

$$y(I)=a_0+a^*\sin(2\pi I/N+\theta_0)=a_0+a^*\cos\theta_0^*\sin(2\pi I/N)+a^*\sin\theta_0^*\cos(2\pi I/N)=a_0+a_1^*\sin(2\pi I/N)+a_2^*\cos(2\pi I/N) \quad \text{(Equation 2)}$$

$$a=\sqrt{(a_1^2+a_2^2)} \quad \text{(Equation 3);}$$

Once sine wave amplitude a is known, the lean of the container can be calculated by the following equation:

$$\text{Lean}=a^*\text{Container Height/Diameter} \quad \text{(Equation 4).}$$

If the calculated lean exceeds a predetermined amount, then the container is deemed a "leaner" and is rejected.

Use of the least square fitting technique above requires some initial knowledge of the sine wave, such as the sine cycle N. The least square fitting calculations and analysis of the resulting sine wave described above are oftentimes quite time consuming, especially if an exhaustive search of the sine cycle N is completed. In an effort to minimize the amount of computing time required, an additional technique referred to as a golden section search technique may be employed. The golden section search is a line search method for achieving fast and accurate searching of the sine cycle N, and is only needed during the setup for inspection of a particular bottle design. Once the sine cycle N is found, then it becomes a known parameter in Equation 1. For any container, initial estimations of the sine cycle can be made based on the revolutions per gauge and the number of scan lines in the image (e.g., 72 scan lines in the above example). Once the initial estimations are made, a line search having a golden search ratio of 0.168 is performed over a closed interval. An object of this search is to use multiple iterations to determine a sine cycle N that gives a minimum fitting error.

For example, a first line search iteration involves searching a first range of possible N values that includes golden section points $N_1$ and $N_2$. This first range begins at a "start" value, extends along a line through golden section points $N_2$ and $N_1$, in that order, and terminates at an "end" value. The fitting error at $N_1$, referred to as $Q(N_1)$, is compared to the fitting error at $N_2$, referred to as $Q(N_2)$. If $Q(N_1)$ is $\geq Q(N_2)$, then the optimum N value lies along the line between the start point and golden section point $N_1$, if $Q(N_1)$ is $<Q(N_2)$, then the optimum N value lies along the line between golden section point $N_2$ and the end point. Thus, the second line search interval is over either the range start-$N_1$ or $N_2$-nd, both of which are smaller ranges than the first range. The second line search iteration requires selection of new golden section points, as the $N_1$ and $N_2$ values are no longer in the middle of the search range. In the instance where the range of the second search iteration is from start-$N_1$, new golden section points $N_3$ and $N_4$ are selected such that they are within this range and point $N_4$ is equal to $N_2$. Again, fitting errors $Q(N_3)$ and $Q(N_4)$ are calculated for each of the new golden section points; but because point $N_4$ is equal to point $N_2$, only $Q(N_3)$ needs to be calculated. If $Q(N_3)$ is $\geq Q(N_2)$, then the optimum N value lies along the line between golden section point $N_3$ and $N_1$; if $Q(N_3)$ is $<Q(N_2)$, then the optimum N value lies along the line between the start point and golden section point $N_2$. In this manner, each search iteration is over a smaller and smaller range until the process converges on an optimal N value which minimizes the fitting error. Another technique that may be used by the optical inspection apparatus of the present invention to improve the least square fitting method involves the use of Min/Max values. Not all points measured by the optical inspection apparatus are needed to solve Equation 1, as that equation can be accurately solved by selecting only those points within a certain distance of a Min and Max value. In fact, computation of the least square fitting algorithm is quicker with less data points. For example, if a point A represents the maximum point for the height differential curve expressed in Equation 1 and point B represents the minimum point, then this technique selects only those points falling within a predetermined range, say within 15% of the difference between point A and B. The least square fitting method can then be performed on only these points. If this fails to provide enough points for accurate testing, simply increase the percentage to a level that does supply enough points.

There have thus been disclosed an optical inspection apparatus and method for inspecting the bearing surface of a container, which fully satisfy all of the objects and aims previously set forth. Several alternatives and modifications have been described. Other alternatives and modifications will readily suggest themselves to persons of ordinary skill in the art. For example, pre-processor 106 is shown as being included within information processor 56, however, the pre-processor could just as easily be incorporated into light sensor 54 or another appropriate component. Also, incident light line 60 is described as a line of light having a predetermined width W, but it is possible for light source 50 to emit an incident light beam instead. The majority of the discussion above pertains to the inspection of knurled surfaces, however, non-knurled or smooth bearing surfaces could just as easily be inspected. In the case of a smooth bearing surface, either with or without a seating ring, the reflected light beam received by the light sensor would be a continuous beam. The invention is intended to embrace all such alternatives and modifications as fall within the spirit and broad scope of the appended claims.

What is claimed is:

1. Apparatus for inspecting lean of a container having a container bottom, which includes:
    means for holding a container in position and rotating the container around an axis,
    a light source positioned beneath the container in said means for directing light energy onto the bottom of the container,
    a light sensor positioned beneath the container to receive portions of the light energy from said source reflected from the container bottom, and
    an information processor coupled to said light sensor for determining, as a combined function of said reflected light energy and container rotation, departure of the container bottom from a plane perpendicular to said axis.

2. The apparatus set forth in claim 1 wherein said light energy is directed from said source onto a periphery of the container bottom and said information processor determines departure of the periphery of the container bottom from said plane perpendicular to said axis.

3. The apparatus set forth in claim 2 wherein the container includes knurling around the periphery of the container bottom, and said image processor is responsive to said reflected light energy to determine depth of said knurling.

4. The apparatus set forth in claim 1 wherein said information processor includes a preprocessor for scanning said light sensor at first increments of container rotation, and a main processor for receiving scan data from said preprocessor at second increments of container rotation greater than said first increments.

5. The apparatus set forth in claim 1 wherein said means for holding the container in position and rotating the container around an axis includes spaced backup rollers for externally engaging the container, and a drive roller for engaging and rotating the container while holding the container against said backup rollers so as to define an average axis of rotation as a function of geometry of the container and spacing between said backup rollers.

6. The apparatus set forth in claim 1 comprising two of said light sources and two of said light sensors positioned in pairs on diametrically opposed sides of said axis, said information processor being responsive to a comparison of outputs of said light sensors to indicate lean of a container.

7. The apparatus of claim 1 for inspecting a container bottom surface having a plurality of knurls, wherein the knurls cause said light sensor to receive non-continuous reflections from a knurl peak and a knurl valley.

8. The apparatus of claim 7, wherein said sensor output signal at least includes first outputs representing reflections from the knurl peak and second outputs representing reflections from the knurl valley.

9. The apparatus of claim 8, wherein said information processor is adapted to utilize said first outputs to determine container lean.

10. The apparatus of claim 8, wherein said information processor is adapted to utilize both said first and second outputs to determine knurl depth.

11. The apparatus of claim 1, wherein said information processor is adapted to generate a sinusoidal expression representative of a height differential between two positions on the container bottom.

12. The apparatus of claim 11, wherein said information processor uses a least square fitting technique to derive values for one or more variables of said sinusoidal expression.

13. The apparatus of claim 12, wherein said derived values are used to determine container lean.

14. The apparatus of claim 12, wherein said information processor uses an iterative search method for determining a sine cycle for said sinusoidal expression.

15. The apparatus of claim 14, wherein said iterative search method is a golden section search.

16. The apparatus of claim 12, wherein said information processor uses a selection process involving Min/Max data points to improve the efficiency of the least square fitting technique.

17. A method of inspecting a container bearing surface, comprising the steps of:
    (a) providing a light source generally facing the bearing surface,
    (b) providing a light sensor generally facing the bearing surface,
    (c) rotating the container about an axis,
    (d) causing said light source to emit light which reflects off of a position on the bearing surface,
    (e) causing said light sensor to record the position at which the light reflected in said step (d) strikes said light sensor, and
    (f) analyzing from said position data recorded in said step (e) departure of the bearing surface from a plane perpendicular to said axis.

18. The method of claim 17, wherein the bearing surface being inspected is a knurled surface.

19. The method of claim 17, wherein step (e) further includes compressing data from said recorded position data.

20. The method of claim 17, wherein step (f) further includes utilizing a sinusoidal expression to model the bearing surface of the container.

21. The method of claim 20, wherein one or more variables of said sinusoidal expression are solved using a least square fitting technique.

* * * * *